(12) United States Patent  
Halmann et al.

(10) Patent No.: US 7,115,093 B2  
(45) Date of Patent: Oct. 3, 2006

(54) METHOD AND SYSTEM FOR PDA-BASED ULTRASOUND SYSTEM

(75) Inventors: Menachem Halmann, Milwaukee, WI (US); Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 428 days.

(21) Appl. No.: 10/063,342

(22) Filed: Apr. 12, 2002

(65) Prior Publication Data

US 2003/0097071 A1 May 22, 2003

Related U.S. Application Data

(60) Provisional application No. 60/332,023, filed on Nov. 21, 2001.

(51) Int. Cl.  
*A61B 8/00* (2006.01)

(52) U.S. Cl. .................. 600/437; 600/443
(58) Field of Classification Search ........... 600/437, 600/440–450, 453–456, 4; 128/916, 921–2; 73/625–626; 702/127  
See application file for complete search history.

(56) References Cited

U.S. PATENT DOCUMENTS 5,930,744 A * 7/1999 Koch et al. ............... 702/170
6,106,472 A   8/2000 Chiang et al.
6,440,072 B1* 8/2002 Schuman et al. .......... 600/437
6,464,636 B1* 10/2002 Kinicki et al. ............. 600/437
6,475,146 B1* 11/2002 Frelburger et al. ........ 600/437
6,482,158 B1* 11/2002 Mault ....................... 600/437
6,497,661 B1* 12/2002 Brock-Fisher ............. 600/437
6,569,097 B1*  5/2003 McMorrow et al. ....... 600/437
6,610,012 B1*  8/2003 Mault ....................... 600/437
6,635,019 B1* 10/2003 Davidsen ................... 600/459
6,716,171 B1*  4/2004 Brock-Fisher ............. 600/443

FOREIGN PATENT DOCUMENTS

JP         20030033350       * 2/2003

* cited by examiner

*Primary Examiner*—Francis J. Jaworski  
(74) *Attorney, Agent, or Firm*—McAndrews, Held & Malloy, Ltd.; Peter J. Vogel; Michael A. Dellapenna

(57) ABSTRACT

A method and system are disclosed for a compact, inexpensive ultrasound system using an off-the-shelf personal digital assistant (PDA) device interfacing to a hand-held probe assembly through a standard digital interface. The hand-held probe assembly comprises a detachable transducer head attached to a beamforming module that performs digital beamforming. The PDA runs Windows applications and displays menus and images to a user. The PDA also runs ultrasound data processing software to support a plurality of imaging modes. An internal battery is provided in the PDA to power the system. The transducer head is detachable from the beamforming module.

25 Claims, 6 Drawing Sheets and # METHOD AND SYSTEM FOR PDA-BASED ULTRASOUND SYSTEM

CROSS REFERENCE TO RELATED APPLICATIONS

The applicants claimed priority based on provisional application No. 60/332,023 filed Nov. 21, 2001 in the names of Nahi Halmann and Shinichi Amemiya.

BACKGROUND OF INVENTION

Certain embodiments of the present invention relate to a medical diagnostic ultrasound scanner. More particularly, certain embodiments relate to a method and system for configuring a personal digital assistant (PDA) device as an integral part of a portable, hand-held ultrasound system.

Traditional ultrasound systems are often large and bulky and do not lend themselves for ease of portability and tend to be expensive. Therefore, traditional ultrasound systems are not practical for certain market segments such as emergency medical personnel in ambulances, medical school students in training, and physicians and nurses at remote locations.

For example, today, emergency medical personnel (EMP) may use a stethoscope to listen to a patient's chest for lung rattles, or abdominal sounds such as bowel noise, or heart murmurs, etc. If equipped with ultrasound, the EMP could see fluid in the lungs, movement of the bowel, or blood flow in the heart. A more portable type of ultrasound system is required for such an application.

Smaller systems exist but are often still too expensive and/or do not provide desired features. For example, in U.S. Pat. No. 6,106,472 to Chiang et al., a portable ultrasound imaging system is described that uses charge coupled device (CCD) technology and performs beamforming in the analog domain. Such an implementation is limited by the specialized CCD technology and by performing beamforming in the analog domain.

It is more desirable to perform beamforming in the digital domain by first converting ultrasound data from the analog domain to the digital domain by, for example, using a simple analog-to-digital converter (ADC). Beamforming in the digital domain provides more flexibility and potentially better accuracy than beamforming in the analog domain.

A need exists for a small, inexpensive, highly portable ultrasound system employing existing technology that may be used quickly and easily for basic diagnosis in emergency situations at remote locations and for training purposes. A need also exists to perform digital beamforming in a highly portable ultrasound system in order increase beamforming flexibility and remove the need for specialized hardware.

SUMMARY OF INVENTION

An embodiment of the present invention provides for a compact, inexpensive ultrasound system using an off-the-shelf, commercially available personal digital assistant (PDA) device interfacing to a signal beamforming module through a standard digital interface. A detachable ultrasound transducer head also interfaces to the beamforming module to form a hand-held probe assembly. The PDA runs Windows applications and displays menus and images to a user. The PDA is also modified to include ultrasound data processing and application software to support a plurality of ultrasound imaging modes. An internal battery is provided in the PDA to power the system. Digital beamforming is performed within the beamforming module by a beamforming ASIC.

A method is provided for attaching a detachable transducer head to a beamforming module to form a hand-held probe assembly that includes the beamforming module and the detachable transducer head. Ultrasound signals are received with the hand-held probe assembly from a region of interest to generate a plurality of received digital signals within the hand-held probe assembly. The plurality of received digital signals are digitally beamformed within the hand-held probe assembly to generate beams of digital data corresponding to the region of interest. The beams of digital data are transmitted to a commercially available personal digital assistant (PDA) over a standard digital interface to be further processed and displayed to a user as a displayed image representing the region of interest.

Certain embodiments of the present invention afford an approach to interface a standard, off-the-shelf, inexpensive PDA device to a hand-held ultrasound probe assembly to provide ultrasound scanning capability that is highly portable and affordable.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
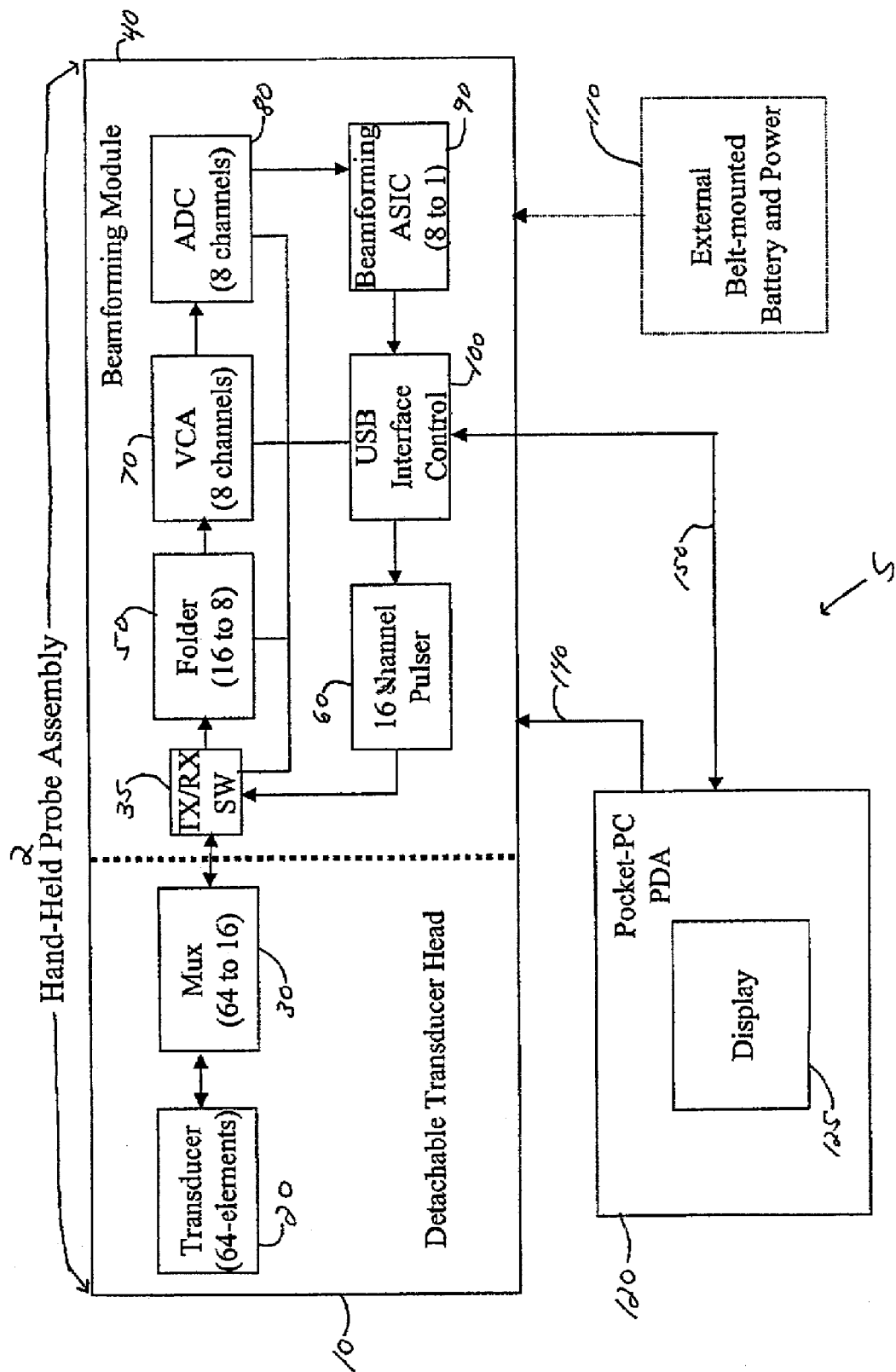
FIG. 1 is a schematic block diagram of a portable diagnostic ultrasound system formed in accordance with an embodiment of the present invention such that digital beamforming is performed within a hand-held probe assembly.
Figure 1B:
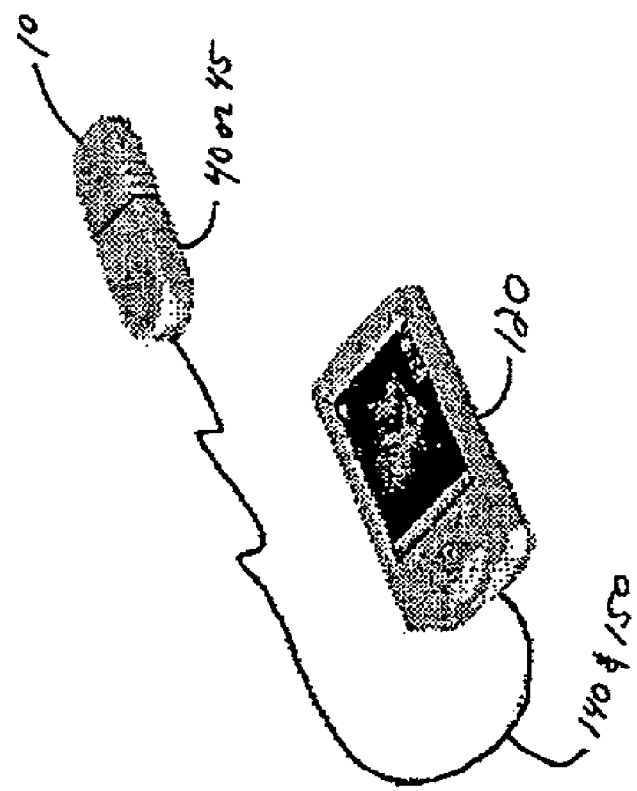
FIG. 1B shows a realistic illustration of the portable diagnostic ultrasound system of FIG. 1.
Figure 1B:
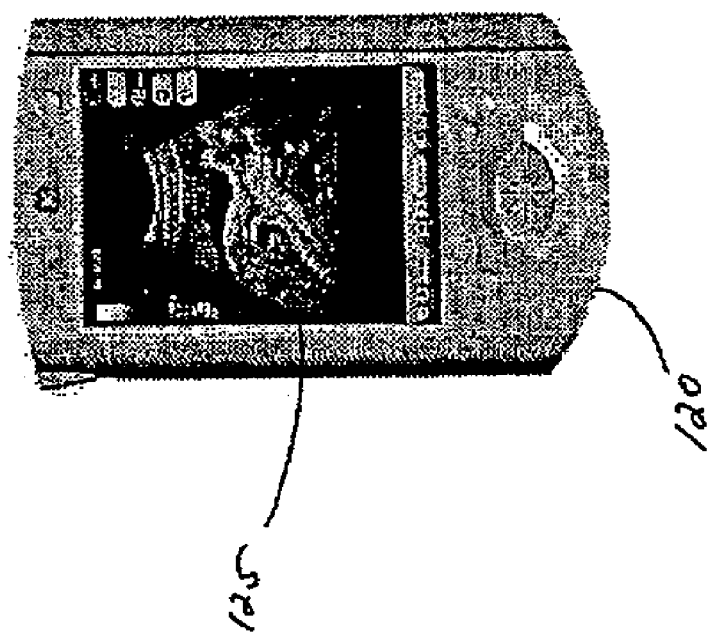

FIG. 1 is a schematic block diagram of a portable ultrasound system 5 in accordance with an embodiment of the present invention. Certain illustrated elements of the ultrasound system 5 include a detachable transducer module 10, a beamforming module 40, a PDA device 120, and, optionally, an external battery/power source 110. The transducer module 10 attaches to the beamforming module 40 to form a hand-held probe assembly 2. In an embodiment of the present invention, the PDA 120 includes an internal battery to power the PDA 120 and the hand-held probe assembly 2. A battery power interface 140 connects between the PDA 120 and the hand-held probe assembly 2. FIG. 1B shows a more realistic illustration of the ultrasound system 5.

The transducer module 10 comprises a 64-element transducer array 20 and a 64 channel to 16 channel multiplexer 30. The beamforming module 40 comprises a pulser 60, a TX/RX switching module 35, a folder module 50, a voltage controlled amplifier (VCA) 70, an analog-to-digital converter (ADC) 80, a beamforming ASIC 90, and a PDA interface controller 100. The PDA device 120 is a standard, off-the-shelf device such as a Palm Pilot running Windows applications such as Windows-CE applications and having a touch-screen display 125. The PDA 120 is also modified to include ultrasound data processing and application software to support a plurality of ultrasound imaging modes.

In the transducer module 10, the transducer array 20 is connected to the multiplexer 30. When the transducer module 10 is connected to the beamforming module 40, the multiplexer 30 is then connected to an input of TX/RX switching module 35.

In the beamforming module 40, the output of the TX/RX switching module 35 connects to the input of the folder module 50 and the output of the folder module 50 connects to the input of the VCA 70. The output of the VCA 70 connects to the input of the ADC 80. The output of the ADC 80 connects to the input of the beamforming ASIC 90. The output of the beamforming ASIC 90 connects to the input of the PDA interface controller 100. The output of the 16-channel pulser 60 connects to an input of TX/RX switching module 35. Optionally, an external battery/power source 110 connects to beamforming module 40.

The PDA interface controller 100 connects to the pulser 60, and to the PDA device 120 through a standard digital interface 150. In an embodiment of the present invention, the standard digital interface 150 is a Universal Serial Bus (USB) interface and the PDA interface controller 100 is a USB controller. Optionally, the standard digital interface 150 may be a parallel interface where the PDA interface controller 100 is a PC card. As a further alternative, the standard digital interface may be a wireless interface such as Bluetooth providing RF communication between the PDA interface controller 100 and the PDA 120.

The various elements of the portable ultrasound system 5 may be combined or separated according to various embodiments of the present invention. For example, the folder 50 and VCA 70 may be combined into a single processing element. Also, the external battery 110 may be integrated into the beamforming module 40, becoming an internal battery.

A function of the PDA-based ultrasound scanner 5 is to transmit ultrasound energy into a subject to be imaged, and receive and process backscattered ultrasound signals from the subject to create and display an image on the display 125 of the PDA device 120. A user selects a transducer head 10 to connect to the beamforming module 40 to form a handheld probe assembly 2 to be used for a particular scanning application. The transducer head is selected from a group of transducers including linear arrays, curved arrays, and phased arrays. An imaging mode may be selected from a menu on the display 125 of the PDA device 120 using a touch-screen stylus.

To generate a transmitted beam of ultrasound energy, the PDA device 120 sends digital control signals to the PDA interface controller 100 within the beamforming module 40 through the standard digital interface 150. The digital control signals instruct the beamforming module 40 to generate transmit parameters to create a beam of a certain shape that originates from a certain point at the surface of the transducer array 20. The transmit parameters are selected in the pulser 60 in response to the digital control signals from the PDA device 120. The pulser 60 uses the transmit parameters to properly encode transmit signals to be sent to the transducer array 20 through the TX/RX switching module 35 and the multiplexer 30. The transmit signals are set at certain levels and phases with respect to each other and are provided to individual transducer elements of the transducer array 20. The transmit signals excite the transducer elements of the transducer array 20 to emit ultrasound waves with the same phase and level relationships as the transmit signals. As a result, a transmitted beam of ultrasound energy is formed in a subject within a scan plane 200 (see FIG. 2) along a scan line 210 when the transducer array 20 is acoustically coupled to the subject by using, for example, ultrasound gel.

In an embodiment of the present invention, a single ultrasound beam is formed along a particular scan line (e.g. 210) using 16 transducer elements. For example, elements 301 through 316 may be used to form a first ultrasound beam along a scan line 210 and elements 302 through 317 may be used to form a second adjacent ultrasound beam along a scan line 212 and so on. As a result, 64 ultrasound beams may be formed to create an image if the transducer array 20 has 64 transducer elements. Alternatively, elements 301 to 316 may be used to form a first ultrasound beam along a scan line 210 and elements 302 through 316 may be used to form a second adjacent ultrasound beam along a scan line 211 and elements 302 through 317 may be used to form a third ultrasound beam along a scan line 212 adjacent to the second ultrasound beam and so on. As a result, 128 ultrasound beams may be formed to create an image if the transducer array 20 has 64 transducer elements. In any event, the pulser 60 sends 16 transmit signals at a time through multiplexer 30 to form a given transmit ultrasound beam along a given scan line. The multiplexer 30 routes the transmit signals to the correct subset of transducer elements in the transducer array 20 to form a particular transmit beam along a particular scan line.

The transducer elements form a two-way transducer array 20. Once ultrasound waves are transmitted into a subject, the ultrasound waves are backscattered off of tissue and blood samples within the structure. The backscattered waves arrive at the transducer array 20 at different times, depending on the distance into the subject they return from and the angle with respect to the surface of the transducer array 20 at which they return. The transducer elements are responsive to the backscattered waves and convert the ultrasound energy from the backscattered waves into received electrical signals.

The received electrical signals are routed through the multiplexer 30, 16 signals at a time, to the folder module 50 by way of the TX/RX switching module 35 in beamforming module 40. The folder module 50 uses the symmetry of the ultrasound beam to process the signals from the 8 right-most transducer elements in the same manner as the signals from the 8 left-most transducer elements since the ultrasound beam originates from the center of 16 transducer elements. The folder module 50 amplifies and weights the received signals and collapses the original 16 received signals into 8 received signals due to the symmetry of the transducer elements about the received beam to be formed.

Next, the received signals are passed to the VCA 70. The VCA 70 provides the function of gain compensation as a function of time (distance into the image). Next, the ADC 80 digitizes the received signals. The beamforming ASIC 90 then takes the digitized received signals and creates a received beam of data along a scan line (e.g. 210). The beamforming ASIC 90 operates on the digitized received signals by performing time delaying and summing to create the received beam of data corresponding to sample volumes along a scan line (e.g. 210) in the scan plane 200 within the subject. The beamforming ASIC 90 is a digital ASIC performing beamforming in the digital domain and providing beamforming flexibility. For example, the beamforming ASIC 90 may be digitally loaded with various beamforming coefficients and instructions from the PDA 120 to perform different types of digital beamforming.

The received beam of digital data is sent to the PDA device 120 by the PDA interface controller 100 over the standard digital interface 150. The process is repeated for the next receive beam to be formed and so on to generate all of the received beams 260 that make up the image frame 250 for the region of interest (see FIG. 3).

The PDA device 120 collects and processes the received beam data for the entire set of received beams 260 that make up an image frame 250 and displays the resultant image to the user on the display 125 of the PDA device 120. The PDA device 120 performs ultrasound data processing including the ultrasound functions of demodulation, parameter estimation, scan conversion, and display processing. A plurality of ultrasound modes may be supported including Doppler processing modes and non-Doppler processing modes.

Frame rates on the order of 10 frames per second may be achieved and the system may consume less than 5 watts of power, allowing for operation over approximately a 2-hour period of time.

Figure 4:
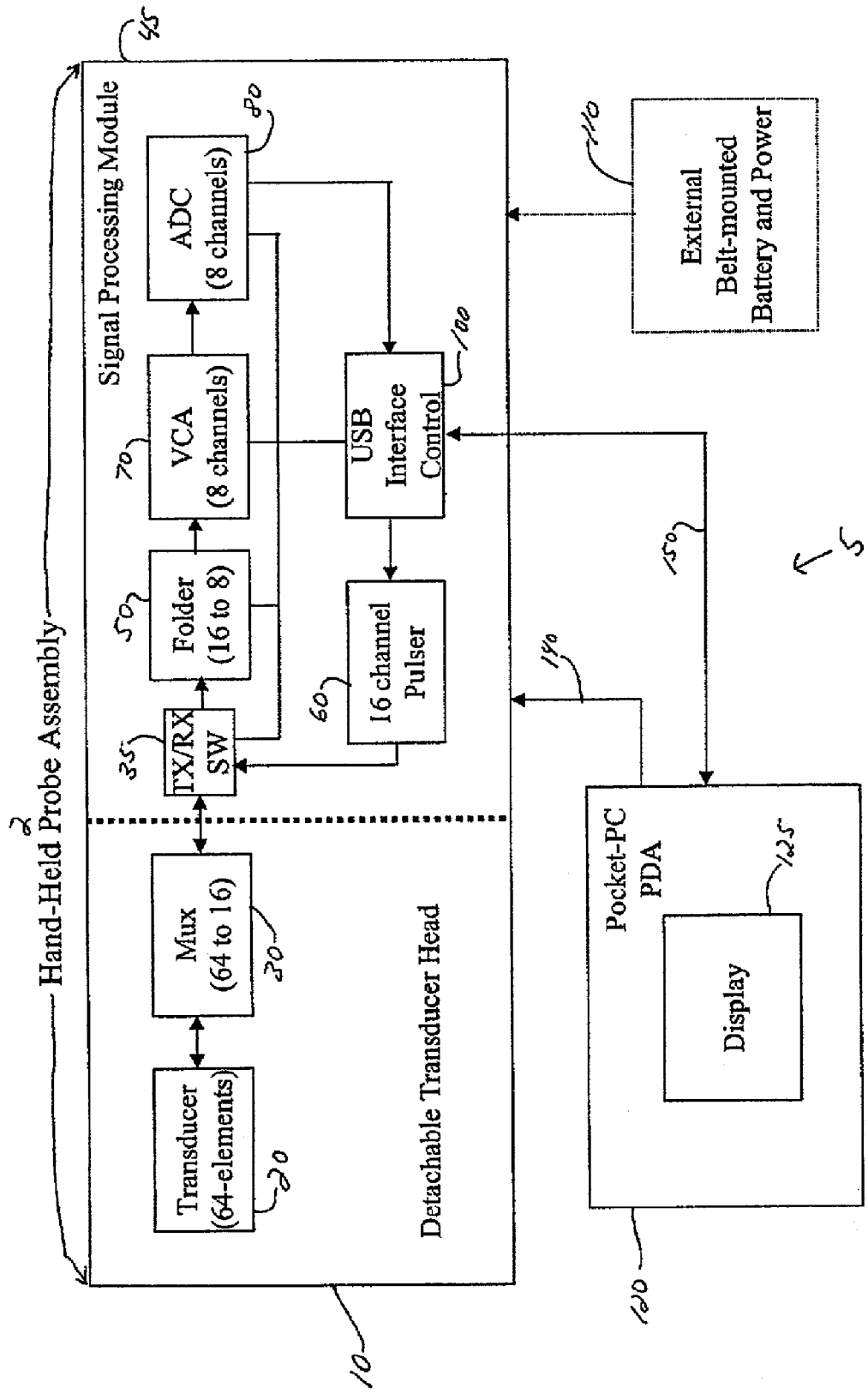
FIG. 4 is a schematic block diagram of a diagnostic ultrasound system formed in accordance with another embodiment of the present invention such that digital beamforming is performed in a PDA device.

As an alternative, the function of the beamforming ASIC 90 may be performed by software in the PDA device 120 as shown in FIG. 4. Instead of the transducer head attaching to a beamforming module 40, it attaches to a signal processing module 45 that does not include the beamforming ASIC 90. The data out of the ADC 80 is sent to the PDA interface controller 100 and the pre-beamformed data is sent to the PDA 120. Digital beamforming is performed by software within the PDA 120 along with the other subsequent data processing functions.

As a further alternative, the hand-held-probe assembly may include an internal battery to provide power. A docking station may also be provided for the hand-held probe assembly to provide the function of battery recharging.

As still a further alterative, the transducer module 10 may be a sterile probe for use in an operating room (OR), such as in a sterile wireless probe assembly.

Figure 5:
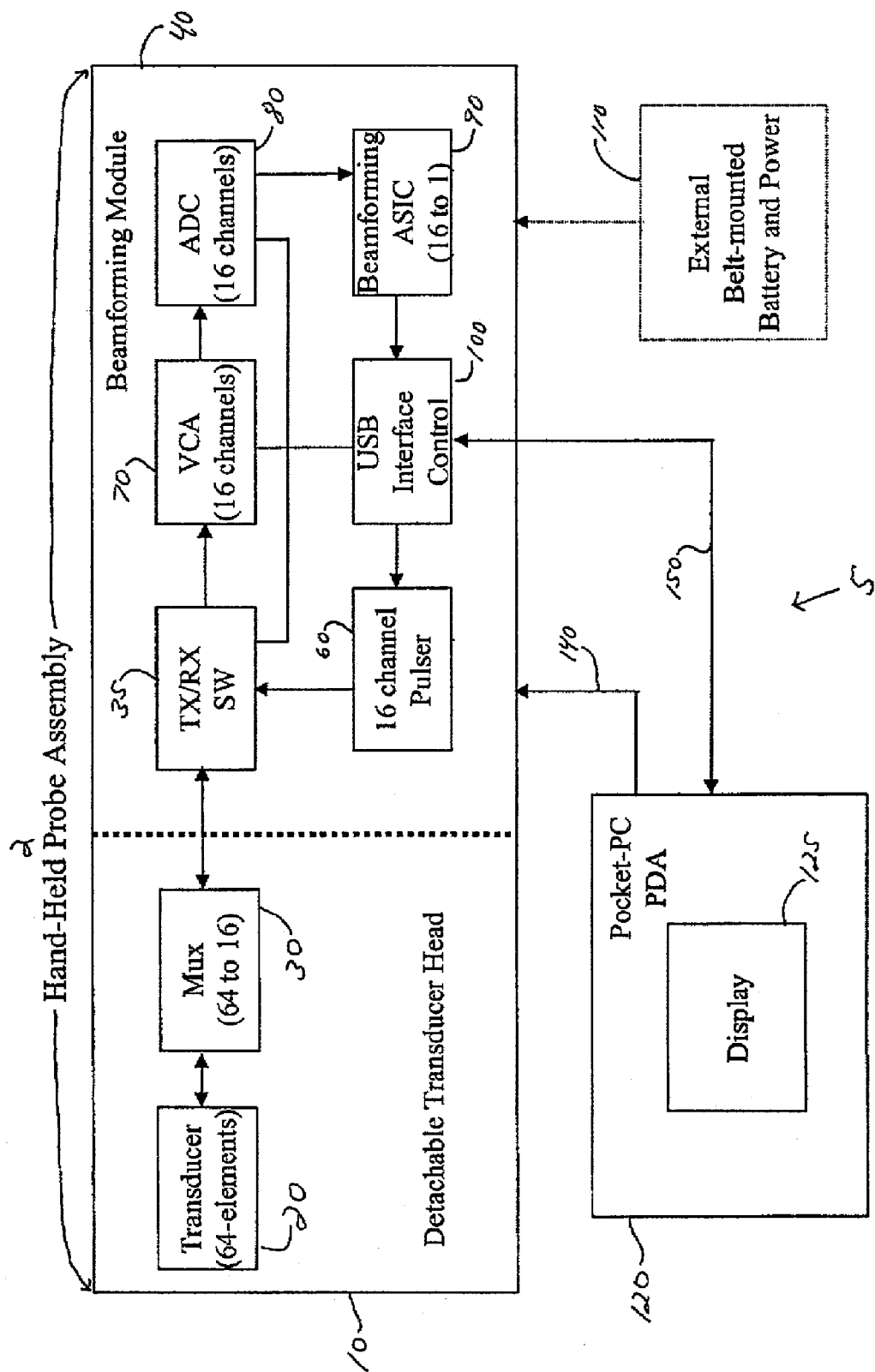
FIG. 5 is a schematic block diagram of a diagnostic ultrasound system formed in accordance with a third embodiment of the present invention.
Figure 1:
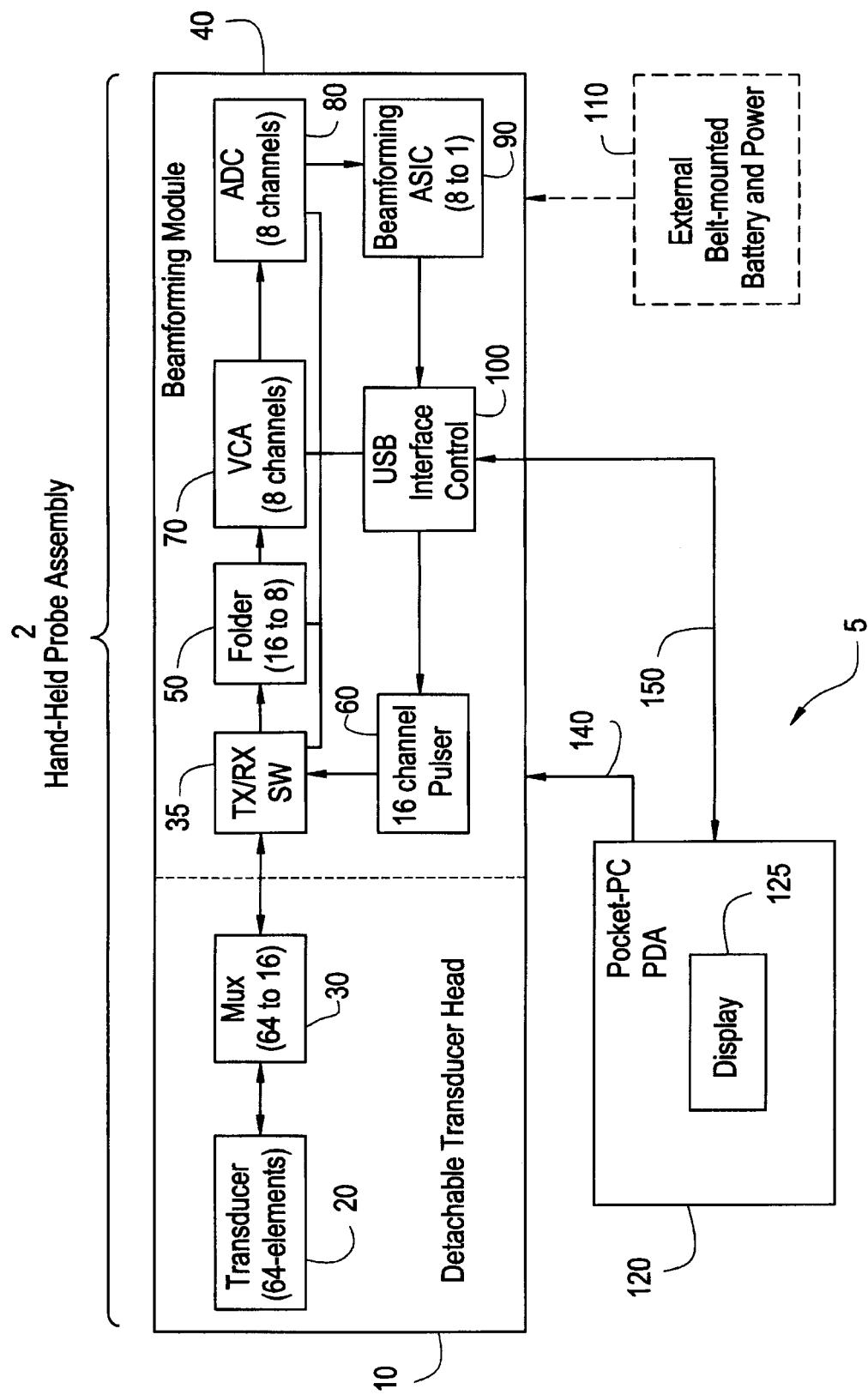
Figure 1B:
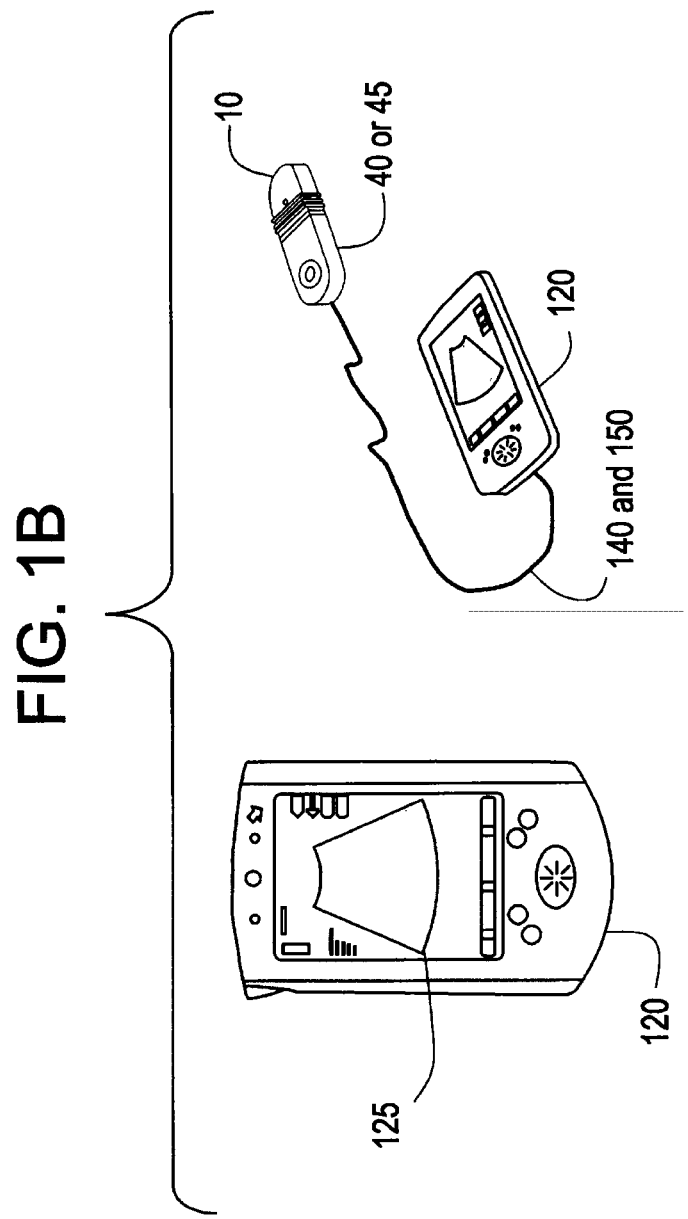
Figure 2:
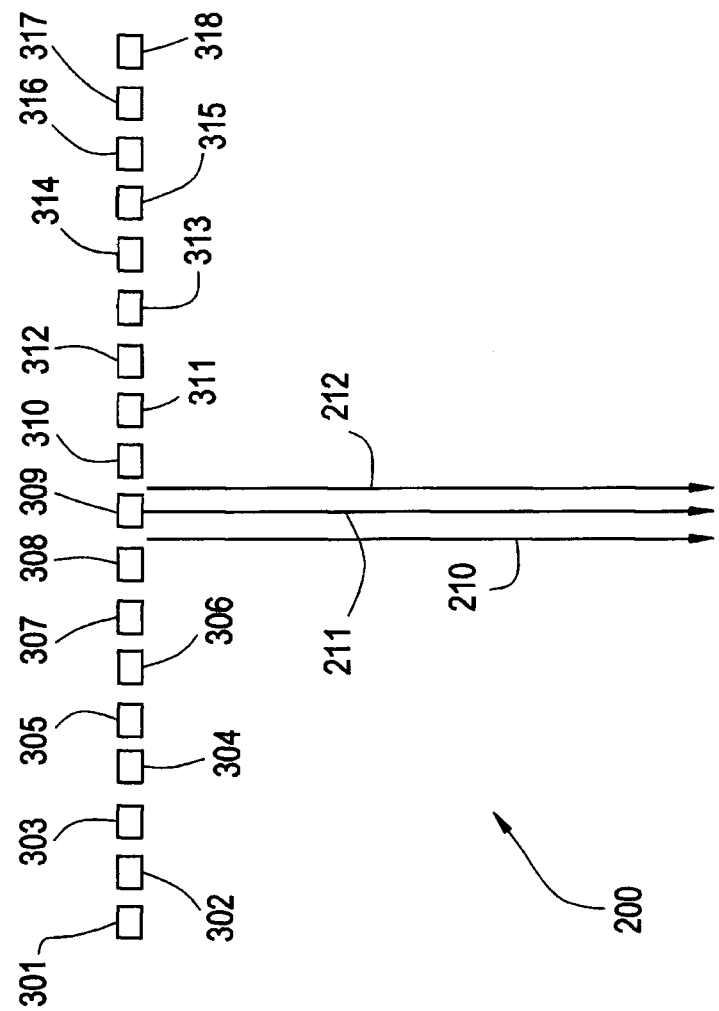
Figure 4:
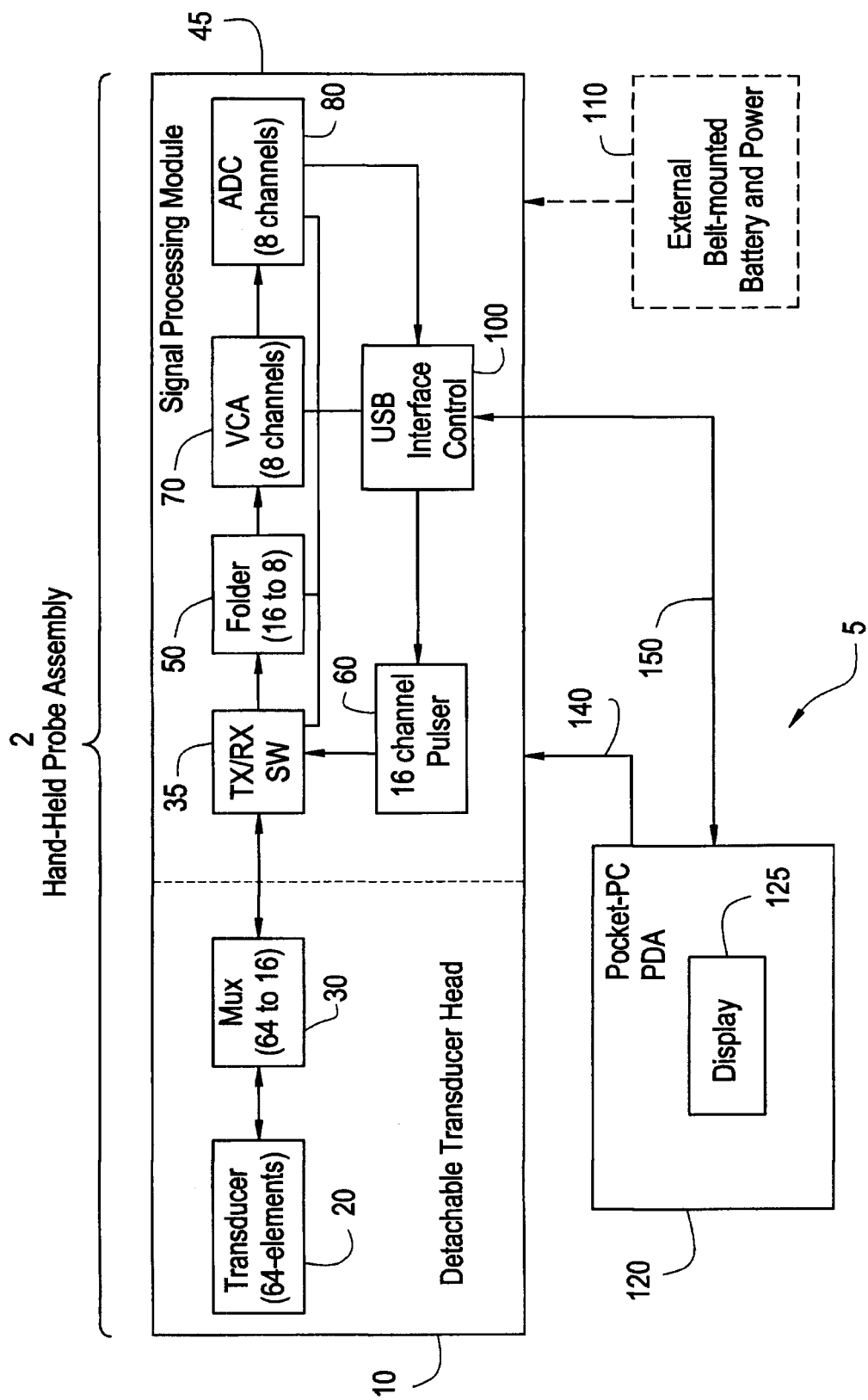
Figure 5:
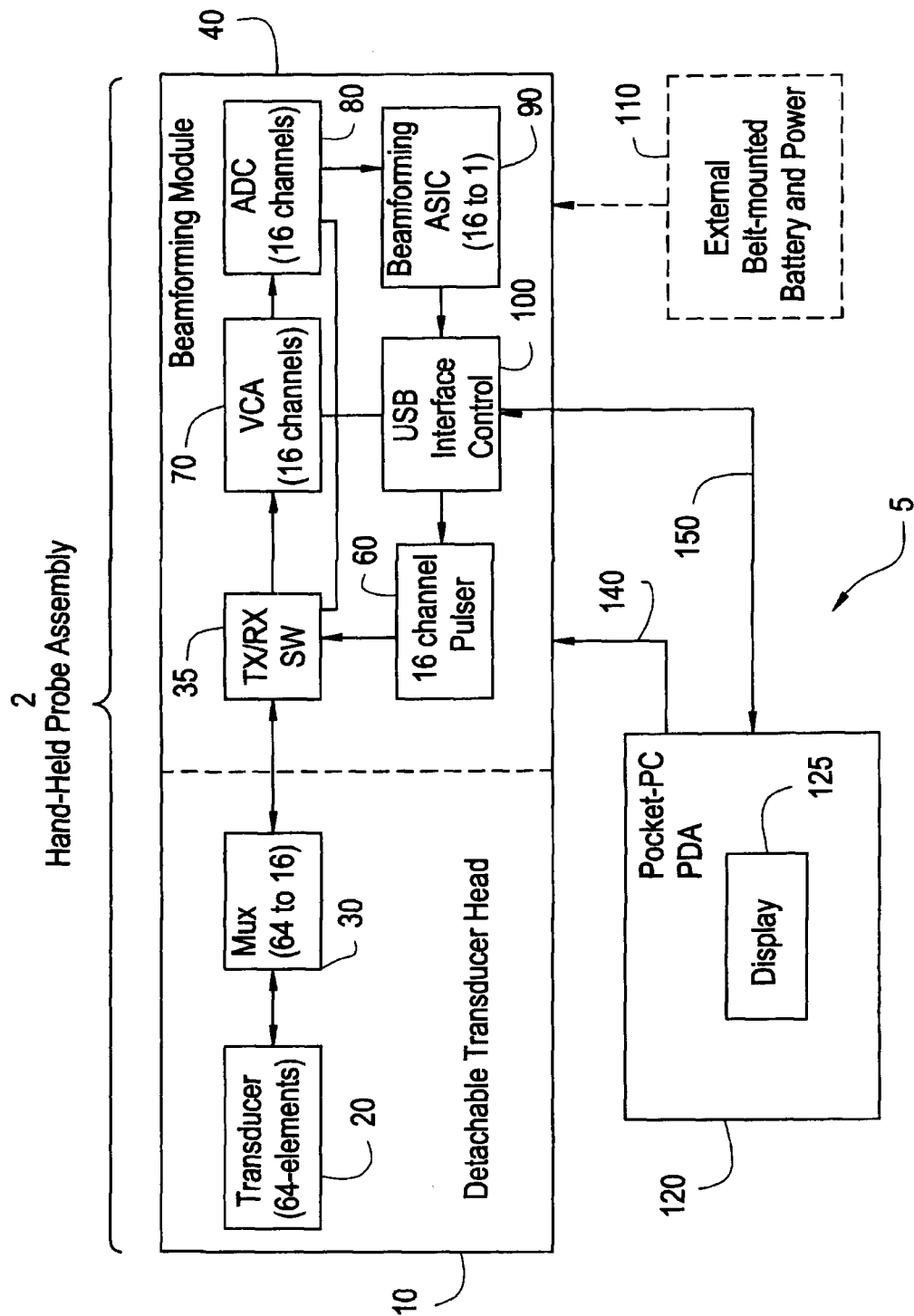

As yet another alternative, the beamforming module (or signal processing module) may be designed to perform 16 bit processing. For example, the folder module 50 may be eliminated and the VCA 70 and the ADC 80 may be designed to handle 16 bits instead of just 8 bits as shown in FIG. 5.

The various configurations and interfaces within the system 5 may be combined or separated according to various embodiments of the present invention. For example, the beamforming module 40 may comprise custom hardware elements such as a small circuit board with digital signal processors or may comprise readily available off-the-shelf components.

In summary, the advantages and features include, among others, a light-weight, portable ultrasound system based on inexpensive, off-the-shelf PDA technology to provide high portability and ease of use for certain users. Digital beamforming provides maximum beamforming flexibility, and a transducer head may be selected from a set of detachable transducer heads to connect to a beamforming or signal processing module to form a hand-held probe assembly. A user may easily change applications by attaching a different transducer head to the beamforming module or signal processing module and/or by selecting a new imaging application on the touch-screen display of the PDA.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

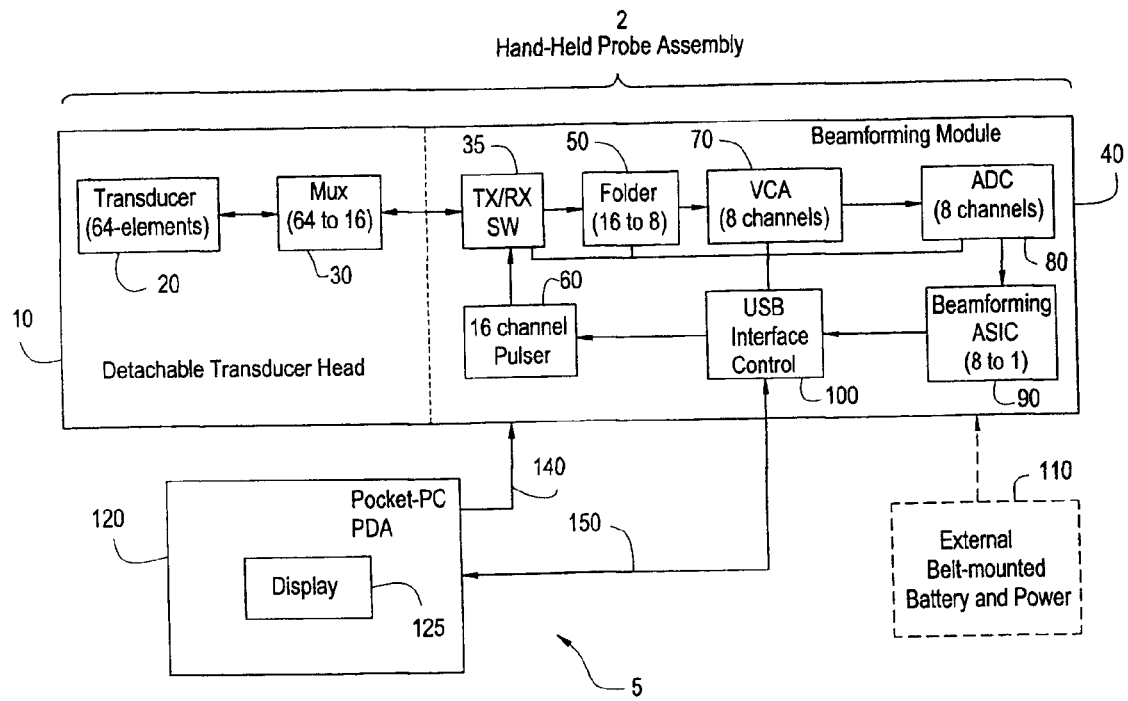

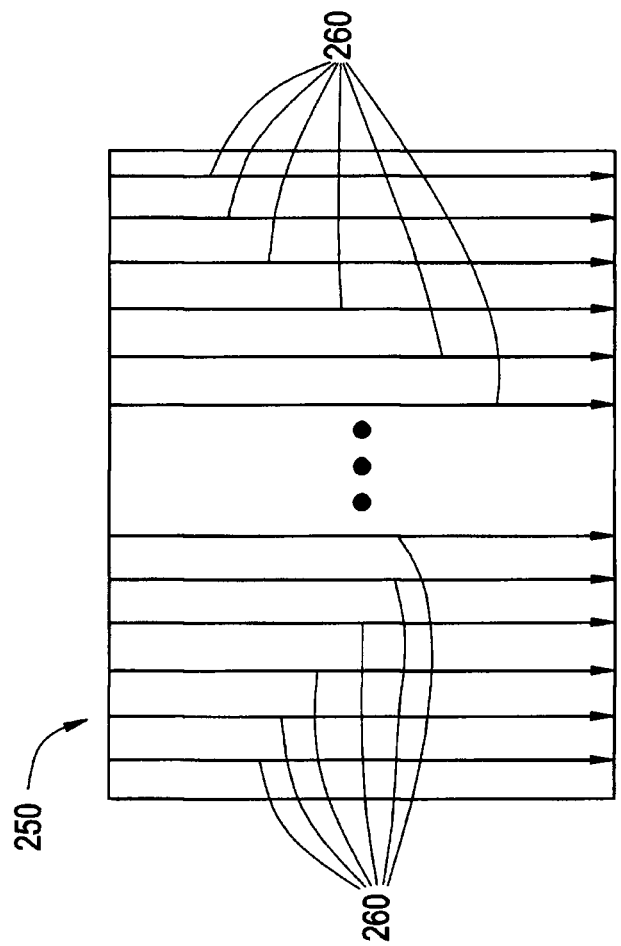

The invention claimed is:

1. A method of ultrasound imaging, said method comprising: attaching a detachable transducer head to a beamforming module to form a hand-held probe assembly that includes said beamforming module and said detachable transducer head; receiving ultrasound signals with said hand-held probe assembly from a region of interest to generate a plurality of received digital signals within said hand-held probe assembly; digitally beamforming said plurality of received digital signals within said hand-held probe assembly to generate at least one beam of digital data corresponding to said region of interest; transmitting said at least one beam of digital data to a commercially available personal digital assistant (PDA) over a standard digital interface, wherein said PDA includes software to perform ultrasound data processing functions including: demodulation, parameter estimation, scan conversion, and display processing.

2. The method of claim 1 wherein said detachable transducer head is selected from a group comprising a linear array transducer, a curved array transducer, and a phased array transducer.

3. The method of claim 1 wherein said ultrasound data processing further comprises: demodulating said at least one beam of digital data, within said PDA, to generate demodulated data; parameter estimating said demodulated data, within said PDA, to generate parameter estimate data; scan converting said parameter estimate data, within said PDA, to generate scan converted data; and display processing said scan converted data, within said PDA, to generate a displayed representation of said region of interest on a display of said PDA.

4. The method of claim 3 wherein said parameter estimating comprises performing Doppler processing.

5. The method of claim 3 wherein said parameter estimating comprises performing non-Doppler processing.

6. The method of claim 1 further comprising transmitting digital control signals from said PDA to said hand-held probe assembly over said standard digital interface.

7. The method of claim 1 wherein said standard digital interface comprises a wireless interface between said hand-held probe assembly and said PDA.

8. The method of claim 1 wherein said standard digital interface comprises a serial link between said hand-held probe assembly and said PDA.

9. The method of claim 1 wherein said standard digital interface comprises a parallel link between said hand-held probe assembly and said PDA.

10. The method of claim 1 further comprising running Windows applications on said PDA to display menus and images to a user.

11. The method of claim 1 wherein said PDA includes ultrasound data processing and application software to support a plurality of ultrasound imaging modes.

12. The method of claim 1 wherein said digitally beamforming includes time delaying and summing said plurality of received digital signals.

13. A system for performing ultrasound imaging, said system comprising: a beamforming module for performing ultrasound signal processing functions including digital beamforming; a detachable transducer head attaching to said beamforming module to form a hand-held probe assembly; and a commercially available personal digital assistant (PDA) connecting to said hand-held probe assembly through a standard digital interface wherein said PDA includes an electronic processor for processing computer software to perform ultrasound data processing functions, including: demodulation, parameter estimation, scan conversion, and display processing.

14. The system of claim 13 wherein said detachable transducer head comprises: a set of transducer elements; and a multiplexer connecting to said set of transducer elements to select and route a first set of received analog signals from a subset of said set of transducer elements to said beamforming module.

15. The system of claim 13 wherein said beamforming module comprises: an analog-to-digital converter (ADC) converting a third set of received analog signals to a first set of received digital signals; a beamforming ASIC connecting to said ADC and generating at least one beam of digital data from said first set of received digital signals; a pulser module generating a set of analog transmit signals in response to digital control data from said PDA and sending said set of analog transmit signals to said transducer head.

16. The system of claim 15 wherein said beamforming module further comprises: a TX/RX switching module to switch between passing said set of analog transmit signals and a first set of received analog signals; a folder module generating a second set of received analog signals from said first set of received analog signals received from said transducer head via said TX/RX switching module; a voltage controlled amplifier (VCA) connecting to said folder module and generating said third set of received analog signals from said second set of received analog signals; and a digital interface controller connecting to said beamforming ASIC and transmitting said at least one beam of digital data to said PDA and receiving said digital control data from said PDA over said standard digital interface.

17. The system of claim 13 wherein said PDA includes a touch-screen display for displaying ultrasound image data and menus generated by said system.

18. The system of claim 13 wherein said standard digital interface comprises a serial link.

19. The system of claim 13 wherein said standard digital interface comprises a parallel link.

20. The system of claim 13 wherein said standard digital interface comprises a wireless link.

21. The system of claim 13 wherein said PDA includes an internal battery that powers said PDA and said hand-held probe assembly.

22. The system of claim 13 further comprising an external battery connecting to said hand-held probe assembly to power said hand-held probe assembly.

23. The system of claim 13 further comprising a battery power interface connecting between said PDA and said hand-held probe assembly.

24. The system of claim 13 wherein said hand-held probe assembly includes an internal battery to power said hand-held probe assembly.

25. The system of claim 13 further comprising a docking station to plug said hand-held probe assembly into for charging a battery of said hand-held probe assembly.

* * * * *

UNITED STATES PATENT AND TRADEMARK OFFICE
CERTIFICATE OF CORRECTION

PATENT NO.         : 7,115,093 B2
APPLICATION NO.    : 10/063342
DATED              : October 3, 2006
INVENTOR(S)        : Halmann et al.

It is certified that error appears in the above-identified patent and that said Letters Patent is hereby corrected as shown below:

On the Title Page, delete drawing and replace with formal drawing FIG. 1

Sheet 1 of 6, delete FIG. 1 and replace with formal drawing FIG. 1

Sheet 2 of 6, delete FIG. 1B and replace with formal drawing FIG. 1B

Figure 2:
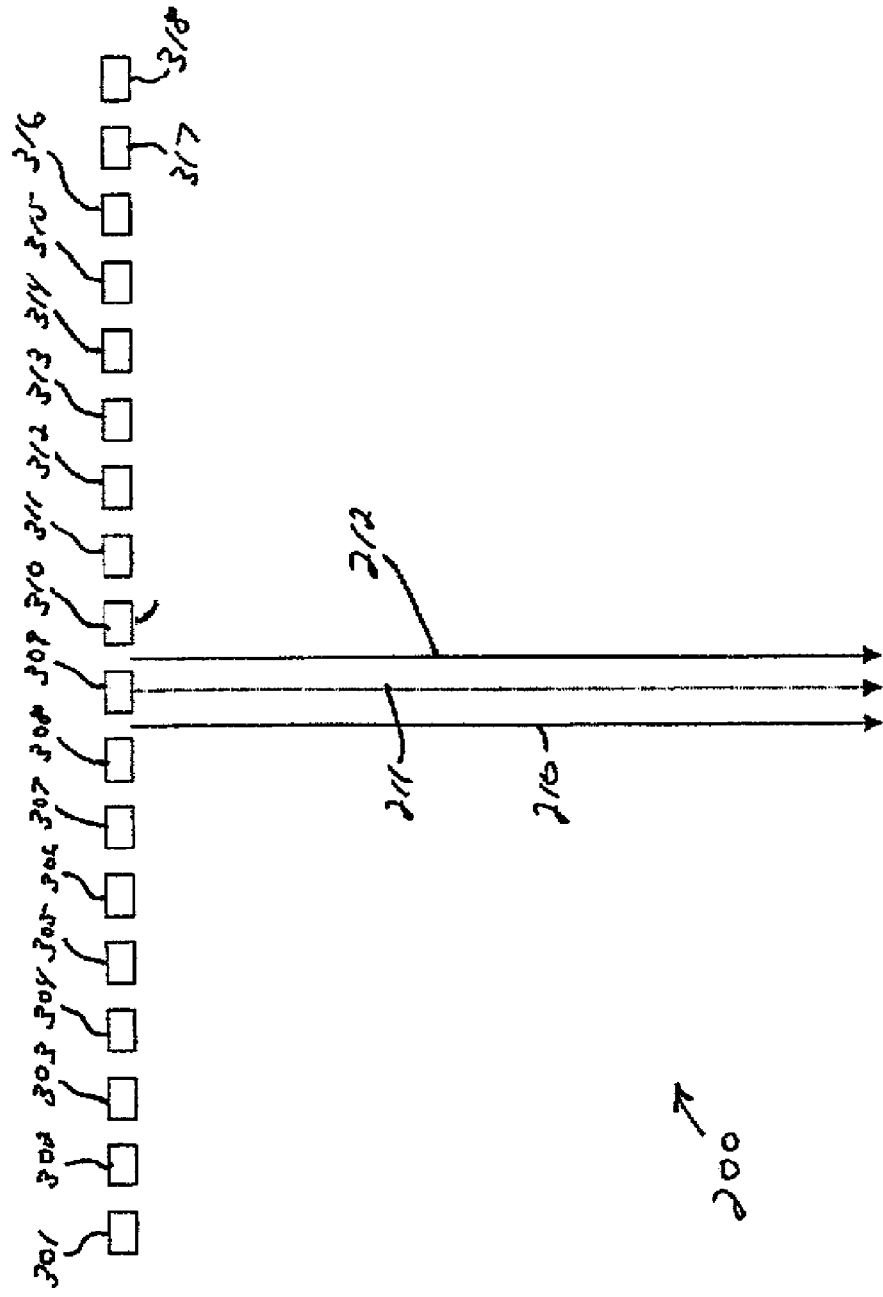
FIG. 2 illustrates the formation of ultrasound beams in a scan plane originating at certain locations with respect to transducer elements in accordance with an embodiment of the present invention.

Sheet 3 of 6, delete FIG. 2 and replace with formal drawing FIG. 2

Figure 3:
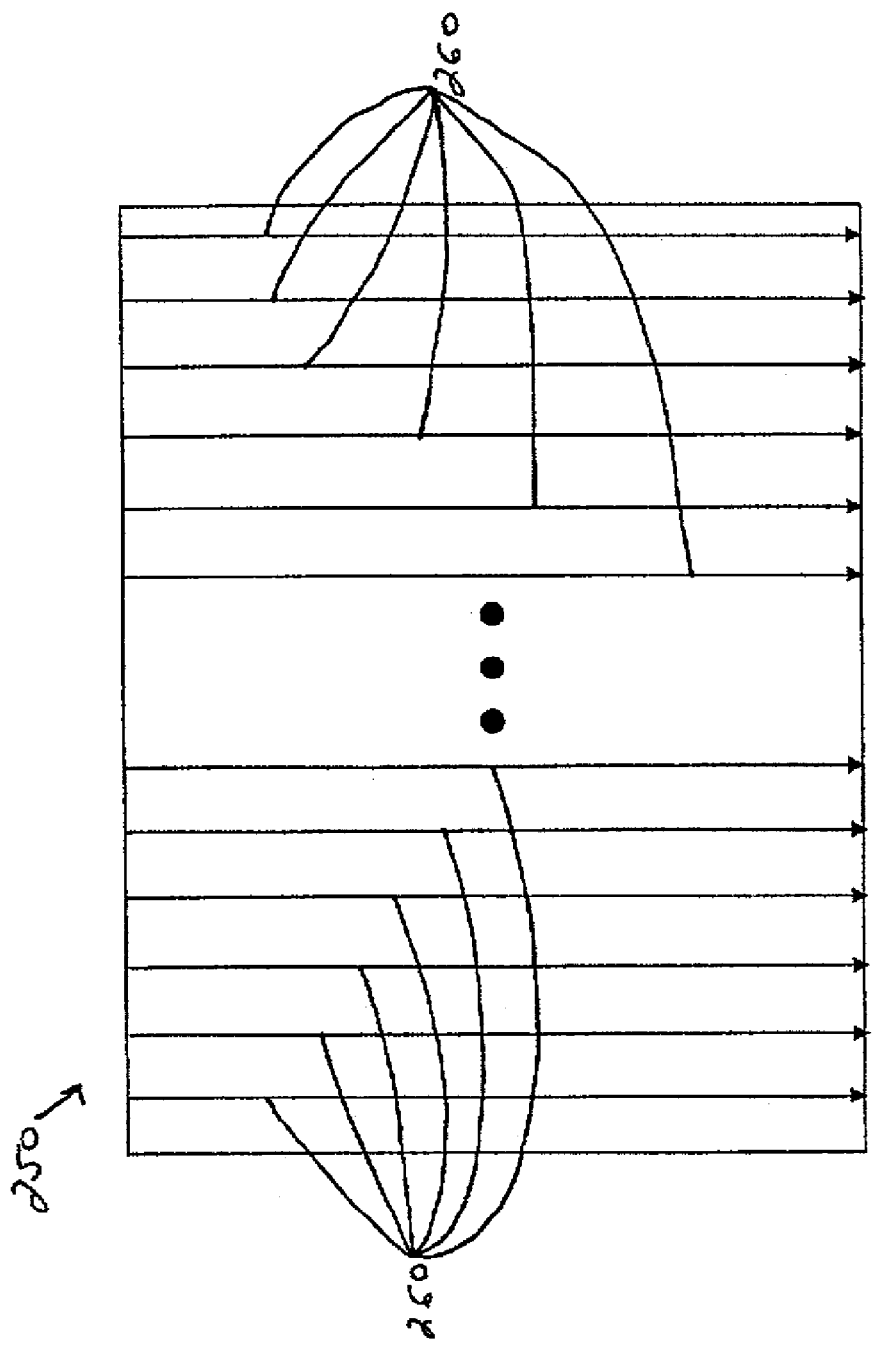
FIG. 3 illustrates an image frame made up of multiple received beams in accordance with an embodiment of the present invention.

Sheet 4 of 6, delete FIG. 3 and replace with formal drawing FIG. 3

Sheet 5 of 6, delete FIG. 4 and replace with formal drawing FIG. 4

Sheet 6 of 6, delete FIG. 5 and replace with formal drawing FIG. 5

See Attached sheets

Signed and Sealed this
Ninth Day of April, 2013

Teresa Stanek Rea
*Acting Director of the United States Patent and Trademark Office*

(12) United States Patent
Halmann et al.

(10) Patent No.: US 7,115,093 B2
(45) Date of Patent: Oct. 3, 2006

(54) METHOD AND SYSTEM FOR PDA-BASED ULTRASOUND SYSTEM

(75) Inventors: Menachem Halmann, Milwaukee, WI (US); Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 428 days.

(21) Appl. No.: 10/063,342

(22) Filed: Apr. 12, 2002

(65) Prior Publication Data
US 2003/0097071 A1    May 22, 2003

Related U.S. Application Data

(60) Provisional application No. 60/332,023, filed on Nov. 21, 2001.

(51) Int. Cl.
*A61B 8/00* (2006.01)
(52) U.S. Cl. .................................... 600/437; 600/443
(58) Field of Classification Search ............... 600/437, 600/440–450, 453–456, 4; 128/916, 921–2; 73/625–626; 702/127
See application file for complete search history.

(56) References Cited

U.S. PATENT DOCUMENTS

| | | | |
|---|---|---|---|
| 5,930,744 A * | 7/1999 | Koch et al. | 702/170 |
| 6,106,472 A | 8/2000 | Chiang et al. | |
| 6,440,072 B1 * | 8/2002 | Schuman et al. | 600/437 |
| 6,464,636 B1 * | 10/2002 | Kinicki et al. | 600/437 |
| 6,475,146 B1 * | 11/2002 | Frelburger et al. | 600/437 |
| 6,482,158 B1 * | 11/2002 | Mault | 600/437 |
| 6,497,661 B1 * | 12/2002 | Brock-Fisher | 600/437 |
| 6,569,097 B1 * | 5/2003 | McMorrow et al. | 600/437 |
| 6,610,012 B1 * | 8/2003 | Mault | 600/437 |
| 6,635,019 B1 * | 10/2003 | Davidsen | 600/459 |
| 6,716,171 B1 * | 4/2004 | Brock-Fisher | 600/443 |

FOREIGN PATENT DOCUMENTS

JP    20030033350    * 2/2003

* cited by examiner

*Primary Examiner*—Francis J. Jaworski
(74) *Attorney, Agent, or Firm*—McAndrews, Held & Malloy, Ltd.; Peter J. Vogel; Michael A. Dellapenna

(57) ABSTRACT

A method and system are disclosed for a compact, inexpensive ultrasound system using an off-the-shelf personal digital assistant (PDA) device interfacing to a hand-held probe assembly through a standard digital interface. The hand-held probe assembly comprises a detachable transducer head attached to a beamforming module that performs digital beamforming. The PDA runs Windows applications and displays menus and images to a user. The PDA also runs ultrasound data processing software to support a plurality of imaging modes. An internal battery is provided in the PDA to power the system. The transducer head is detachable from the beamforming module.

25 Claims, 6 Drawing Sheets